United States Patent [19]
Sleister

[11] Patent Number: 5,968,032
[45] Date of Patent: Oct. 19, 1999

[54] SMOKE EVACUATOR FOR A SURGICAL LASER OR CAUTERY PLUME

[76] Inventor: Dennis R. Sleister, 11 Briarbrook Dr., East Greenwich, R.I. 02818

[21] Appl. No.: 09/050,031

[22] Filed: Mar. 30, 1998

[51] Int. Cl.$^6$ ................................................. A61B 17/00
[52] U.S. Cl. ................................. 606/1; 606/10; 606/34; 606/38; 604/35
[58] Field of Search ................................. 606/1, 10, 13, 606/45, 34, 38, 49; 604/23, 35, 26, 22; 96/397, 113, 403, 418; 55/467; 128/908

[56] References Cited

U.S. PATENT DOCUMENTS

| | | | |
|---|---|---|---|
| 4,642,128 | 2/1987 | Solorzano | 606/1 |
| 4,701,193 | 10/1987 | Robertson et al. | 55/217 |
| 4,735,603 | 4/1988 | Goodson et al. | 604/21 |
| 4,751,501 | 6/1988 | Gut | 340/607 |
| 4,986,839 | 1/1991 | Wertz et al. | 55/274 |
| 5,108,389 | 4/1992 | Cosmescu | 606/10 |
| 5,199,944 | 4/1993 | Cosmescu | 604/26 |
| 5,242,474 | 9/1993 | Herbst et al. | 55/210 |
| 5,254,085 | 10/1993 | Cleveland, Jr. | 604/35 |
| 5,318,516 | 6/1994 | Cosmescu | 604/35 |
| 5,336,218 | 8/1994 | Lihares | 606/10 |
| 5,423,779 | 6/1995 | Yeh | 604/317 |
| 5,456,248 | 10/1995 | Holian et al. | 128/205.12 |
| 5,460,602 | 10/1995 | Shapira | 604/22 |
| 5,520,652 | 5/1996 | Peterson | 604/119 |
| 5,578,000 | 11/1996 | Greff et al. | 604/22 |
| 5,674,219 | 10/1997 | Monson et al. | 604/45 |

*Primary Examiner*—Jeffrey A. Smith
*Assistant Examiner*—Pedro Philogene
*Attorney, Agent, or Firm*—Aquilino, Welsh & Flaxman

[57] ABSTRACT

A surgical smoke evacuator for a surgical laser or cautery plume is disclosed. The evacuator includes collection tubing through which surgical smoke is drawn. The collection tubing has a distal end nozzle where the surgical smoke enters the evacuator. The evacuator also includes a variable vacuum motor coupled to the collection tubing for generating suction pressure at a distal end nozzle of the evacuator to draw smoke from a surgical site. A first filter is provided for removing particulates from smoke flowing through the evacuator. The first filter is in fluid communication with the distal end nozzle of the evacuator and the variable motor. A first sensor is attached to the first filter for detecting tissue invagination and a pressure relief device is associated with the evacuator for reducing the suction pressure within the evacuator when the first sensor senses tissue invagination. Finally, the evacuator includes a flow control mechanism interfaced with the first sensor for varying the operation of the variable vacuum motor according to the status of the first filter.

20 Claims, 3 Drawing Sheets

SMOKE EVACUATOR FOR A SURGICAL LASER OR CAUTERY PLUME

BACKGROUND OF THE INVENTION

1. Field of the Invention

The invention relates to a smoke evacuator used for a surgical laser or cautery plume. More particularly, the invention relates to a smoke evacuator having an increased number of interactive controls enabling the evacuator to adjust operating conditions based on sensed backpressure and to immediately reduce vacuum pressure by activating a solenoid relief valve when the evacuator senses tissue invagination.

2. Description of the Prior Art

Laser surgery and cauterization are widely used and accepted medical procedures. During these procedures, the energy of the laser vaporizes tissue onto which the beam is directed. The vaporized tissue becomes what is referred to as "smoke". This smoke must be removed from the surgical area because of sanitary concerns affecting the patient and the medical staff. The smoke must also be removed so that the medical staff has a clear view of the surgical area. The medical staff generally removes the smoke from the surgical area by using a suction device, a small vacuum pump, known as a smoke evacuator.

Most present-day smoke evacuators include several lengths of hose, a nozzle at the surgery end of a hose, a motor or pump that produces suction through the nozzle and hoses, a plurality of filters for removing particulates and potentially harmful materials from the smoke flowing through the tubes, and a manual control for adjusting the suction force produced by the motor or pump.

In operation, a user maneuvers the nozzle around the surgical site, directing the nozzle toward the area of smoke, while controlling the suction power of the motor or pump. Occasionally, the evacuator nozzle becomes obstructed by a surgical object or tissue. This is commonly referred to as tissue invagination.

When the evacuator nozzle becomes obstructed, the user typically has two options. First, the user may pull the nozzle away from the tissue. However, when the user does this, the user runs the risk of damaging the tissue. Alternately, the user may manually reduce the suction of the evacuator or wait for the evacuator to sense the invagination and automatically reduce the suction. Once the suction is reduced, the tissue is released from the nozzle. However, the suction is not immediately reduced to zero, and the tissue may be damaged while the suction gradually decreases.

Another problem experienced by present-day smoke evacuators occurs when one or more of the filters becomes obstructed by liquid and solid particulate matter removed from the surgical site. When a filter becomes partially or fully obstructed, the suction capability of the evacuator is reduced. Therefore, the evacuator is not performing as well as possible, and the suction should be increased to compensate for the loss of performance of the filter. The user must, however, be notified of the loss of suction due to an obstructed filter if the user is to manually increase the suction provided by the evacuator or replace the filters to remove the obstruction. Similarly, the evacuator must be notified of the loss of pressure if the suction is to be increased automatically.

The suction pressure should continuously be monitored to ensure that the operator is properly and accurately informed when an obstruction is detected. Many evacuators monitor the suction, but only provide notice to the operator when the filter is completely obstructed and must be replaced. Other evacuators monitor the suction, and increase or decrease the motor or pump speed in discrete steps as required to keep the suction at a constant level. However, these evacuators do not vary the motor or pump speed while considering other variables, such as the diameter of the suction hose being used with the evacuator. Consequently, the variation in motor or pump speed is not always accurate enough to hold the suction pressure at a constant level.

Considering the state of the prior art, a need exists for a laser smoke evacuator capable of continuously monitoring the differential pressure across a filter, while considering variables of equipment being used with the evacuator, such that the motor or pump speed may be automatically adjusted to maintain a constant suction pressure at the nozzle. Additionally, a need exists for an evacuator providing a continuous display of the state of the filter, such that one using the evacuator has sufficient notice when the filter must be replaced. Finally, a need exists for a laser smoke evacuator capable of sensing tissue invagination and reacting immediately to release the tissue by activating a relief valve to release suction at the nozzle and by transmitting a signal to turn off the motor or pump until the tissue has been released. The present invention provides such an evacuator.

SUMMARY OF THE INVENTION

It is, therefore, an object of the present invention to provide a surgical smoke evacuator for a surgical laser or cautery plume. The evacuator includes collection tubing through which surgical smoke is drawn. The collection tubing has a distal end nozzle where the surgical smoke enters the evacuator. The evacuator also includes a variable vacuum motor coupled to the collection tubing for generating suction pressure at a distal end nozzle of the evacuator to draw smoke from a surgical site. A first filter is provided for removing particulates from smoke flowing through the evacuator. The first filter is in fluid communication with the distal end nozzle of the evacuator and the variable motor. A first sensor is attached to the first filter for detecting tissue invagination and a pressure relief device is associated with the evacuator for reducing the suction pressure within the evacuator when the first sensor senses tissue invagination. Finally, the evacuator includes a flow control mechanism interfaced with the first sensor for varying the operation of the variable vacuum motor according to the status of the first filter.

It is also an object of the present invention to provide a smoke evacuator wherein the first sensor measures the differential pressure across the first filter.

It is a further object of the present invention to provide a smoke evacuator including a second filter proximal the first filter for removing particulates from smoke flowing through the evacuator. The second filter is in fluid communication with the distal end nozzle of the evacuator, the variable motor and the first filter.

It is another object of the present invention to provide a smoke evacuator including a second sensor attached to the second filter for detecting obstruction of the second filter, wherein the flow control mechanism is interfaced with the first sensor and the second sensor for varying operation of the variable vacuum motor according to the status of the first filter and the second filter.

It is also an object of the present invention to provide a smoke evacuator wherein the second sensor includes a proximal second sensor member and a distal second sensor member located on opposite sides of the second filter.

It is a further object of the present invention to provide a smoke evacuator including an indicator interfaced with the first sensor for providing an indication of the first filter status.

It is another object of the present invention to provide a smoke evacuator wherein the pressure relief device is a solenoid relief valve.

It is also an object of the present invention to provide a smoke evacuator wherein the pressure relief device is located between the first filter and the second filter.

It is a further object of the present invention to provide a smoke evacuator wherein the pressure relief device is located between a muffler of the variable vacuum motor and the proximal side of the first filter, between the first filter and the second filter, such that when tissue invagination is detected and the pressure relief device is opened, positive air is pushed into the collection tubing to accelerate the release of the suction.

It is another object of the present invention to provide a smoke evacuator wherein the flow control mechanism, when activated by the first sensor, varies the speed of operation of the motor and activates the pressure relief device, thereby eliminating suction pressure through the distal end nozzle at the surgical site.

It is also an object of the present invention to provide a smoke evacuator wherein the first sensor includes a proximal first sensor member and a distal first sensor member located on opposite side of the first filter and the flow control mechanism varies operation of the variable vacuum motor according to the status of the first filter.

It is a further object of the present invention to provide a smoke evacuator wherein the flow control mechanism, when activated by the first sensor, varies the speed of operation of the variable motor to maintain suction pressure at a constant level.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limited, but merely as the basis for the claims and as a basis for teaching one skilled in the art how to make and/or use the invention.

Figure 1:
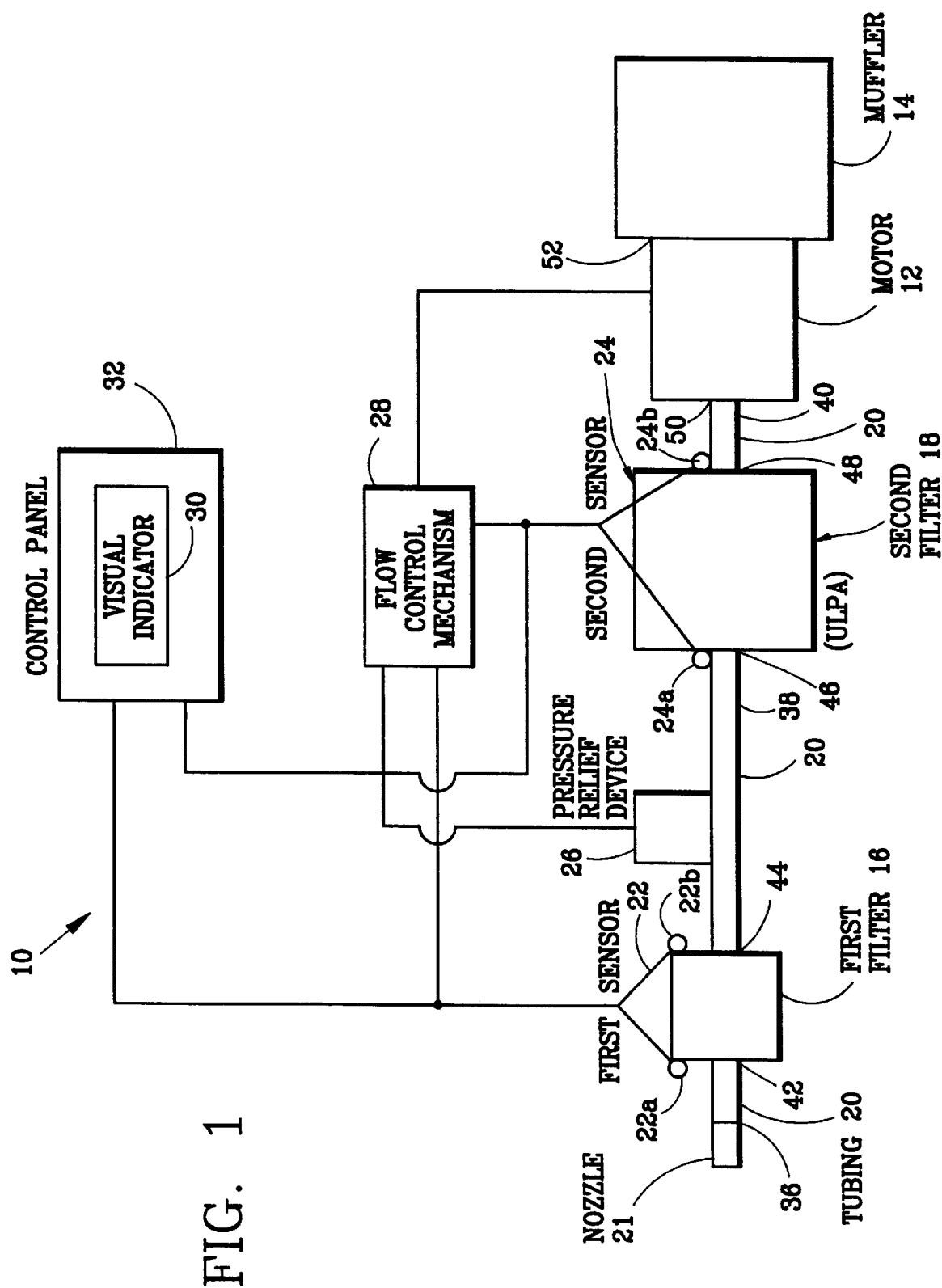
FIG. 1 is a schematic of the present surgical smoke evacuator.

With reference to FIG. 1, the preferred embodiment of the smoke evacuator 10 for a surgical laser or cautery plume is disclosed. As seen in that figure, the evacuator 10 includes collection tubing 20 through which surgical smoke is drawn. A variable vacuum motor 12 is coupled to the collection tubing 20 for generating suction pressure at the distal end nozzle 21 of the evacuator 10. In use, the distal end nozzle 21 is positioned adjacent the surgical site of the patient such that the smoke created by the medical procedure is forced into the distal end nozzle 21 by the suction force of the motor 12. A muffler 14 is attached to the variable vacuum motor 12 and expels air that has been pumped through the evacuator 10.

The evacuator 10 also includes a first filter 16 and a second filter 18. A first sensor 22 is attached to the first filter 16 and a second sensor 24 is attached to the second filter 18. The evacuator 10 further includes a flow control mechanism 28 which receives sensed status signals from the first sensor 22 and the second sensor 24.

The flow control mechanism 28, based on the received signals and the tubing size, provides flow control commands to the variable vacuum motor 12 in manner that will be discussed in greater detail below. The flow control mechanism 28 also provides operating commands to a pressure relief device 26 based on signals received from the first sensor 22 in a manner that will also be discussed below in greater detail.

Finally, the evacuator 10 includes a visual indicator 30 interfaced with the first sensor 22 and second sensor 24. The visual indicator 30, which is mounted on a control panel 32, provides the operator with a constant display of the status of the first filter 16 and the second filter 18.

Specifically, and with reference to FIG. 1, the evacuator 10 provides the operator with precise operating control and indications. The variable motor 12 provides a constant, predetermined suction pressure at the distal end nozzle 21 of the evacuator tubing 20. The distal end nozzle 21 may be provided with a narrow nozzle, a collection shroud, or other types of smoke collection inlets without departing from the spirit of the present invention. The diameter of the collection tubing 20 may be varied to suit specific applications without departing from the spirit of the present invention.

Referring again to FIG. 1, the distal end nozzle 21 is located adjacent the surgical site of the patient such that the smoke created by the medical procedure is forced into the distal end nozzle 21 by the suction force of the motor 12. The smoke enters the distal end nozzle 21 of the tubing 20 and flows through a first section of tubing 36 to the distal end 42 of the first filter 16.

The smoke enters the distal end 42 of the first filter 16 and flows through the first filter 16 which removes particulates and potentially harmful materials from the smoke. The smoke then flows out the proximal end 44 of the first filter 16 into a second section of tubing 38. While flowing through the first filter 16, the pressure of the smoke at the first filter 16 is sensed by a first sensor 22. Preferably, the first sensor 22 is a differential sensor having a distal first sensor member 22a at the distal end 42 of the first filter 16 and a proximal first sensor member 22b at the proximal end 44 of the first filter 16. The first sensor 22 measures the differential pressure across the first filter 16.

After exiting the first filter 16 and entering the second section of tubing 38, the smoke flows toward the second filter 18. The smoke flows into the distal end 46 of the second filter 18 and through the second filter 18. The second filter 18 is preferably an ultra low penetration air filter (ULPA), although other filters could be used without departing from the spirit of the present invention. The smoke exits the second filter 18 through the proximal end 48 of the second filter 18, where it enters a third section of tubing 40.

Attached to the second filter 18 is a second filter sensor 24. Like the first filter sensor 22, the second filter sensor 24 is preferably a differential pressure sensor having a distal second sensor member 24a at the distal end 46 of the second filter 18 and a proximal second sensor member 24b at the proximal end 48 of the second filter 18. The second sensor 24 measures the differential pressure across the second filter 18.

Once the smoke has entered the third section of tubing 40, it has been thoroughly filtered by the first filter 16 and the second filter 18. The filtered smoke is drawn through the third section of tubing 40 and enters the variable vacuum motor 12 at the distal end 50 of the variable vacuum motor 12. The variable vacuum motor 12 passes the filtered smoke through the motor 12 and expels the filtered smoke through the muffler 14 attached to the proximal end 52 of the motor 12.

While the evacuator 10 is operating, the first sensor 22 continuously monitors the status of the first filter 16 by measuring the differential pressure across the first filter 16. The first sensor 22 collects filter status information from the first filter 16 and transmits the information to the flow control mechanism 28. The flow control mechanism 28, based upon the filter status information received from the first sensor 22, provides operating control instructions to the pressure relief device 26 and the variable vacuum motor 12. The first sensor 22 is used to determine when the first filter 16 is partially or fully obstructed. Additionally, the first sensor 22 detects when the distal end nozzle 21 is obstructed by human tissue or a medical device, such as a sponge. This type of obstruction, known as tissue invagination, may damage the human tissue, causing unnecessary harm to the patient.

When the first sensor 22 and the flow control mechanism 28 detect tissue invagination, the flow control mechanism 28 immediately sends a control signal to the variable vacuum motor 12 and to the pressure relief device 26. The motor control signal causes the variable motor 12 to immediately turn off, discontinuing the suction pressure provided by the variable vacuum motor 12. However, because of the time it takes for the motor to wind down, the suction pressure at the distal end nozzle 21 is not instantly reduced to zero pressure. Therefore, the flow control mechanism 28 simultaneously sends a control signal to the pressure relief device 26 to assist with the process of eliminating the suction pressure at the nozzle 21.

The control signal sent by the flow control mechanism 28 to the pressure relief device 26 immediately activates the pressure relief device 26 to open and vent the tubing 20. The pressure relief device 26 is preferably a solenoid relief valve located adjacent the proximal end 44 of the first filter 16, between the first filter 16 and the second filter 18. When the solenoid relief valve is activated, the pressure at the nozzle 21 immediately drops to zero, thus releasing the invaginated tissue held by the nozzle 21.

Figure 2:
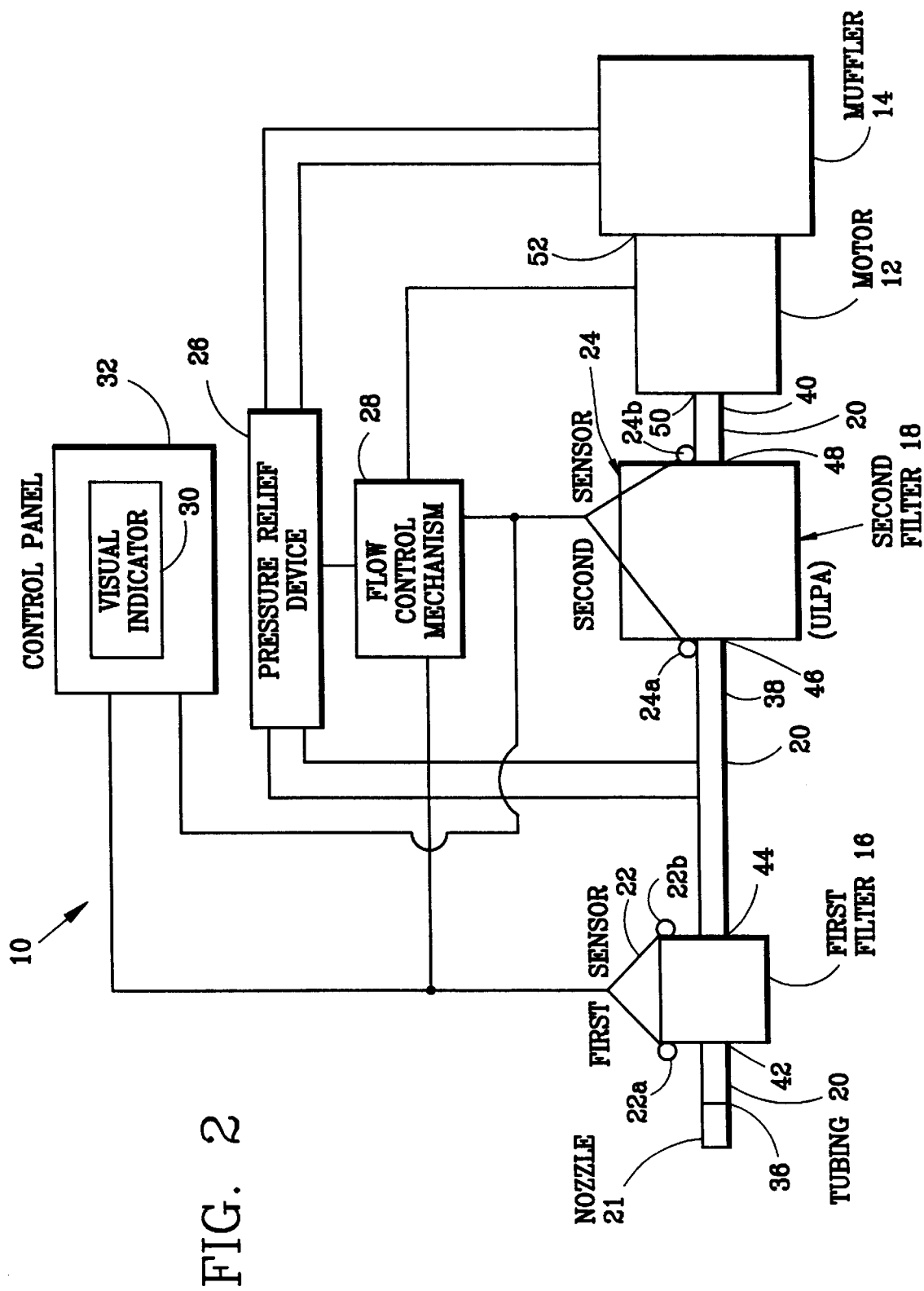
FIG. 2 is a schematic of an alternate embodiment of the present surgical smoke evacuator.

Alternatively, as seen in FIG. 2, the pressure relief device 26 may be connected between the exhaust air stream near the muffler 14 and the distal tubing 36. In accordance with this embodiment, when tissue invagination is sensed, the pressure relief device 26 is activated, but the variable motor 12 is not turned off. When the pressure relief device 26 is activated, a positive air flow is forced into the distal end nozzle 21, thereby forcing the invaginated tissue from the distal end nozzle 21.

In addition to sensing tissue invagination, the first sensor 22 and the flow control mechanism 28 also monitor the operating status of the first filter 16. The flow control mechanism 28 increases or decreases the speed of the variable motor 12, based upon the level of obstruction sensed at the first filter 16, to maintain constant suction pressure at the nozzle 34.

Alternatively, the first sensor 22 can also monitor the absolute pressure on the proximal side 44 of the first filter 16. In this embodiment, the first sensor 22 would measure the absolute pressure over time and monitor the pressure changes.

The evacuator 10 also monitors the status of the second filter 18 via the second sensor 24. The information gathered by the second sensor 24, preferably a differential sensor, is transmitted to the flow control mechanism 28. The evacuator 10 uses this information to determine when the second filter 18 is partially or fully obstructed. The flow control mechanism 28 uses this information to control the variable motor 12 by instructing the motor to change its speed depending upon the level of obstruction sensed at the second filter 18. This also helps to maintain constant suction pressure at the nozzle 21. For example, as the second filter 18 becomes more obstructed, the flow control mechanism 28 instructs the variable motor 12 to increase its speed, thereby holding the suction pressure constant at the nozzle 21.

Information provided by the first sensor 22 and the second sensor 24 is used for more than just controlling the operation of the variable motor 12. Both the first sensor 22 and the second sensor 24 are interfaced with a control panel 32 having a visual indicator 30. The filter sensor signals provided by the first sensor 22 and the second sensor 24 provide information regarding the status of the first filter 16 and the second filter 18, respectively. The control panel 32 and the visual indicator 30 manipulate this information and provide a visual indication of the filter operating status to the evacuator operator. The displayed information provides the operator with a continuous status of the filters and informs the operator when a filter should be replaced. Additionally, the displayed information tells the operator when the first sensor has detected tissue invagination. Therefore, the visual indicator 30 provides the operator with a more interactive method for controlling the operation of the smoke evacuator 10.

Figure 3:
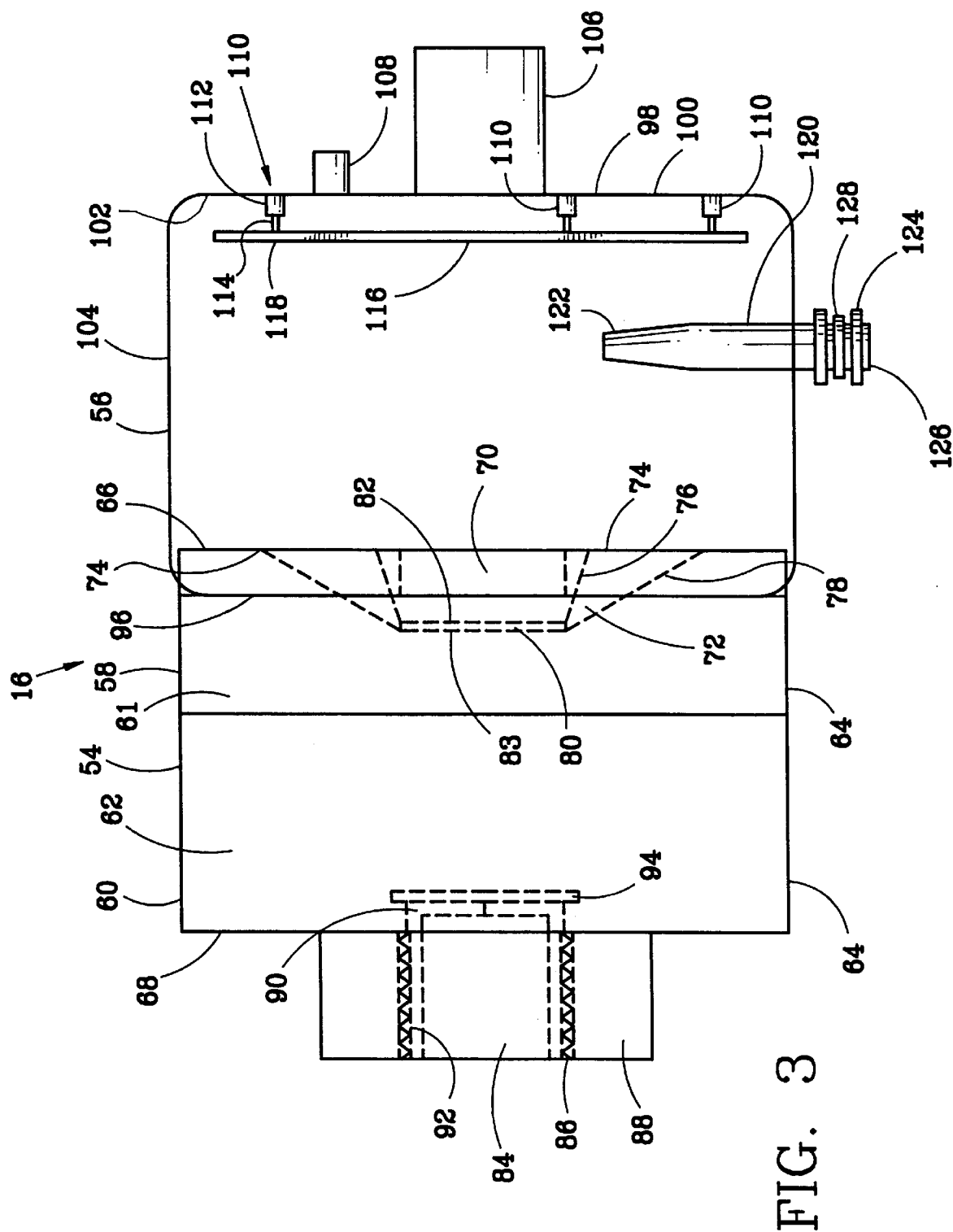
FIG. 3 is a side view of the first filter showing the filter body, the fluid collection cap, and the fluid baffle plate.

With reference to FIG. 3, the detailed construction of the first filter 16 is disclosed. The first filter 16 includes a short, cylindrical filter body 54 manufactured from a high impact styrene material and a fluid collection cap 56 attached to the cylindrical filter body 54. In accordance with the preferred embodiment of the present invention, the fluid collection cap 56 is secured to the filter body 54 with adhesive to ensure that the fluid collection cap 56 and the filter body 54 are not inadvertently disconnected. The filter body 54 is preferably the Racal VER 5, manufactured by Racal Filter Technologies, Inc, although other filter bodies could be used without departing from the spirit of the present invention. While the first filter 56 described below includes a fluid colletion cap 56, the system may employ a filter without a fluid collection cap 56 in applications where fluid is not a concern.

The filter body 54 comprises a first body section 58, a second body section 60 attached to the first body section, and internal filter components 61, 62. The first body section 58 and second body section 60 are each cylindrically shaped and have one open end, one closed end with a port, and a wall. The filter body 54 is assembled by aligning and attaching the open end of the first body section 58 to the open end of the second body section 60, such that the assembled body is a short cylinder-shaped body 54 having an outer wall 64 and two closed ends 66, 68. When assembled, each closed end includes an outer surface, an inner surface and a port.

The port 70 of the first body section 58 is a generally round hole located through the axial center of the closed end of the first body section 58 and has a 0.950 inch diameter. This port functions as the filter body inlet port 70. Eight triangular-shaped support ribs 72 are attached to the inside surface 74 of the closed end 66 of the first body section 58. The support ribs 72 are spaced evenly around the perimeter of the inlet port 70, originating at the perimeter of the inlet port 70 and projecting radially outwardly from the perimeter of the axial center of the inlet port 70. The ribs 72 are positioned in a perpendicular relationship with respect to the inside surface 74 of the closed end 66 of the first body section 58.

Each rib includes 72 a first edge 76 attached to the inside surface 74 of the first body section 58, a second edge 76 projecting downwardly from the perimeter of the filter inlet port 70 toward the center of the filter body 54, and a third edge 78 running radially outwardly and upwardly from the bottom of the second edge 76. The third edge 78 terminates at the inner surface of the closed end 66 of the first body section 58 at a point corresponding with the outermost end of the first edge of the rib 72.

A circular, flat flow diverting plate 80 is located inside and in a concentric relationship with the inlet port 70 of the first body section 58. The flow diverting plate 80 has a diameter approximately equal to the diameter of the inlet port 70. The perimeter of the flow diverting plate 80 is attached to the bottom ends of the second edge 76 of the eight support ribs 72. The flow diverting plate 80 is positioned such that the flat surface area of the plate is perpendicular to the support ribs 72. The first upper surface area 82 of the flow diverting plate 80, in combination with the support ribs 72, evenly distribute air flow within the filter body 54.

The second body section 60 includes an outlet port 84 located at the axial center of the closed end 68 of the second body section 60. The outlet port 84 functions as a filter body outlet port 84 and includes a circular projection 86 which is connected to the second section of tubing 38. The projection 86 has a 1.5 inch threaded outer diameter and extends approximately 0.75 inches outwardly from the outer surface 89 of the closed end 68 of the second body section 60. Threaded onto the threaded projection 86 is a foam gasket 88 which provide an air-tight seal when the first filter 16 is attached to the second section of tubing 38.

The projection 86 is structurally supported by eight support ribs 90. The support ribs 90 originate at the axial center of the outlet port 84, extend radially outwardly from the center, and terminate at the inner surface 92 of the projection 86. In addition to the support ribs 90 located in the outlet port 84, the second body section 60 also includes a perforated filter plate 94 covering the outlet port 84. The perforated filter plate 94 has a diameter equal to the inner diameter of closed end 68. The perforated filter plate 94 is attached to the inner perimeter of the filter outlet port 84 and also to the inner edges of the eight support ribs 90 of the second body section 60.

The cylindrical body 54 of the filter assembly 16, when assembled, encases two filter components 61, 62, assembled in a layered manner. The first component 61, located inside the inlet port 70 adjacent the inner surface 83 of the flow diverting plate 80, is comprised of a micro-filament paper having a pleat height of 1.125 inches. The paper is positioned such that the pleats are perpendicular to the surface area of the flow diverting plate 80. The paper filter occupies the entire cross-sectional area of the filter body 54. Positioned adjacent the pleated paper filter, between the pleated filter and the perforated flow diverting plate 94 is a 12×30 mesh activated charcoal filter 62. The charcoal filter 62 also occupies the entire cross-sectional area of the filter body 54. While various preferred filter media are disclosed above, other filter media could be used without departing from the spirit of the present invention.

The fluid collection cap 56 is cylindrically shaped and includes one open end 96, one flat closed end 98 having an outer surface 100 and an inner surface 102, a wall 104 projecting perpendicularly from the perimeter of the flat closed end 98, and a pressure sensor port 106 located on the wall 104 of the collection cap 56. The collection cap 56 has an inner diameter approximately equal to the outer diameter of the first body section 58, such that the collection cap 56 may be press-fit over the outer wall 64 of the first body section 58 and adhesively sealed to the outer wall 64 of the first body section 58. The wall 104 of the collection cap 56 is slightly thicker near the open end 96 of the collection cap 56, thereby providing a reinforced perimeter 104 which is press-fit over the first body section 58 of the filter body 54. The fluid collection cap 56 is preferably manufactured from Zylar, a composite material comprising copolymerized styrene, butadiene, and methyl methacrylate, although other materials could be used without departing from the spirit of the present invention.

A plurality of cap inlet ports 106, 108 are integrally formed as part of the closed end 98 of the fluid collection cap 56. The diameter of each cap inlet port differs from the diameter of the other cap inlet port, thereby enabling the first filter 16 to be connected to first sections of tubing 36 having differing diameters. In the preferred embodiment, a first cap inlet port 106 having a 0.875 inch or a 1.25 inch outer diameter is positioned at the axial center of the closed end 98 of the fluid collection cap 56. If the 0.875 inch first cap inlet port 106 is employed, it will extend perpendicularly outwardly approximately 1.375 inches from the outer surface 100 of the closed end 98 of the fluid collection cap 56. Additionally, the preferred cap includes a second cap inlet port 108 located such that the axial center of the second cap inlet port 108 is approximately 1.25 inches from the axial center of the closed end 98 of the collection cap 56. The second cap inlet port 108 has an outer diameter of 0.25 inches and extends perpendicularly outwardly approximately 0.5 inches from the outer surface 100 of the closed end 98 of the fluid collection cap 56. The cap inlet ports are designed such that a first section of tubing 36 having the proper inner diameter may be attached to the port by sliding the end of the tubing over the appropriate cap inlet port 106, 108.

In addition to the cap inlet ports 106, 108, the closed end 98 of the fluid collection cap 56 includes three fluid cap mounting pins 110 integrally formed with the inner surface 102 of the closed end 98 of the fluid collection cap 56. The three mounting pins 110, which project from the inner surface 102 of the closed end 98 of the fluid collection cap 56, are spaced equally at a distance of 1.75 inches from the axial center of the closed end 102 of the fluid collection cap 56. Each mounting pin 110 is 0.375 inches long and includes two pin sections, each with a different diameter.

The first pin section 112, originating at the inner surface 102 of the closed end 98 of the fluid collection cap 56, is 0.1875 inches in diameter and extends 0.1875 inches outwardly from the inner surface 102 of the closed end 98, toward the open end 96 of the collection cap 56. The second pin section 114, 0.08975 inches in diameter, originates at the end of the first pin section 112 and extends 0.1875 inches in the same direction as the first pin section 112, toward the open end 96 of the collection cap 56.

As seen in FIG. 3, a fluid baffle plate 116 is attached to the fluid cap mounting pins 110 within the fluid collection cap 56. The fluid baffle plate 116 is a round flat plate with a diameter slightly smaller than the inner diameter of the collection cap 56. The fluid baffle plate 116 is also manufactured from Zylar, a composite material comprising copolymerized styrene, butadiene, and methyl methacrylate. The fluid baffle plate 116 includes three mounting holes 118 aligned and sized for connection to the three fluid cap mounting pins 110.

In operation, as air and waste materials enter either of the cap inlet ports 106, 108, the air and waste is deflected by the baffle plate 116. Thus, the baffle plate 116 prevents fluid from directly entering the filter body 54 and striking the filter input port flow deflection plate 80 and internal filter component 61. The air and waste entering the cap inlet port 106, 108, are deflected by the fluid baffle plate 116, and flow over the surface and perimeter of the baffle plate 116. The air and smaller waste particles continue through the filter inlet port 70 of the first body section 58 of the filter 16. The air flows through filter 16 and out the second body section outlet port 84, while the smaller waste particles are trapped by the filter media 61, 62. The larger waste particles and fluids remain in the fluid collection cap 56.

The fluid collection cap 56 also includes a pressure sensor port 120 integrally formed with the wall 104 of the collection cap 56. The sensor port 120 is comprised of a tube-like structure tangentially positioned with respect to and through the wall 104 of the collection cap 56. The tube-like structure has a proximal end 122 at the wall 104 and a distal end 124 at the end of the tube which is not attached to the collection cap wall 104. The sensor port 120 also includes a membrane 126 located at the distal end 124 of the tube.

When a pressure sensor is inserted into the pressure sensor port 120, the sensor ruptures the membrane 126 and the membrane 126 prevents fluid from flowing out of the fluid collection cap 56 past the sensor and through the pressure sensor port 120. A rubber gasket 128 is positioned about the pressure port sensor 120. The rubber gasket 128 provides a sealed connection between the outer surface of the pressure sensor port 120 and the inner surface of a pressure sensor sleeve when a pressure sensor is attached to the fluid collection cap 56 via the pressure sensor port 120.

While the preferred embodiments have been shown and described, it will be understood that there is no intent to limit the invention by such disclosure, but rather, is intended to cover all modifications and alternate constructions falling within the spirit and scope of the invention as defined in the appended claims.

I claim:

1. A surgical smoke evacuator for a surgical laser or cautery plume, comprising:
   collection tubing through which surgical smoke is drawn, the collection tubing having a distal end nozzle where the surgical smoke enters the evacuator;
   a variable vacuum motor coupled to the collection tubing for generating suction pressure at a distal end nozzle of the evacuator to draw smoke from a surgical site;
   a first filter for removing particulates from smoke flowing through the evacuator, the first filter is in fluid communication with the distal end nozzle of the evacuator and the variable motor;
   a first sensor attached to the first filter for detecting tissue invagination;
   a pressure relief device associated with the evacuator for reducing the suction pressure within the evacuator when the first sensor senses tissue invagination; and
   a flow control mechanism interfaced with the first sensor for varying the operation of the variable vacuum motor according to the status of the first filter.

2. The smoke evacuator according to claim 1, wherein the first sensor measures the differential pressure across the first filter.

3. The smoke evacuator according to claim 1, further including a second filter proximal the first filter for removing particulates from smoke flowing through the evacuator, the second filter is in fluid communication with the distal end nozzle of the evacuator, the variable motor and the first filter.

4. The smoke evacuator according to claim 3, further including a second sensor attached to the second filter for detecting obstruction of the second filter, wherein the flow control mechanism is interfaced with the first sensor and the second sensor for varying operation of the variable vacuum motor according to the status of the first filter and the second filter.

5. The smoke evacuator according to claim 1, further including an indicator interfaced with the first sensor for providing an indication of the first filter status.

6. The smoke evacuator according to claim 1, wherein the pressure relief device is a solenoid relief valve.

7. The smoke evacuator according to claim 1, wherein the pressure relief device is located adjacent the distal end nozzle of the evacuator.

8. The smoke evacuator according to claim 1, wherein the pressure relief device is located between a muffler of the variable vacuum motor and the distal end nozzle adjacent the surgical location, such that when tissue invagination is detected and the pressure relief device is opened, positive air is pushed into the collection tubing to accelerate the release of the suction.

9. The smoke evacuator according to claim 1, wherein the flow control mechanism, when activated by the first sensor, varies the speed of operation of the motor and activates the pressure relief device, thereby eliminating suction pressure through the distal end nozzle at the surgical site.

10. The smoke evacuator according to claim 1, wherein the first filter includes: a filter body having a filter inlet port, a filter outlet port, and an internal filter medium; and a fluid collection cap attached to the filter body and having a fluid baffle plate, a plurality of cap inlet ports, and a pressure sensor port.

11. A surgical smoke evacuator for surgical laser or cautery plume, comprising:
   collection tubing through which surgical smoke is drawn, the collection tubing having a distal end nozzle where the surgical smoke enters the evacuator;
   a variable vacuum motor coupled to the collection tubing for generating suction pressure at a distal end nozzle of the evacuator to draw smoke from a surgical site;
   a first filter for removing particulates from smoke flowing through the evacuator, the first filter is in fluid communication with the distal end nozzle of the evacuator and the variable motor;
   a first sensor attached to the first filter for detecting obstructions within the first filter, the first sensor including a proximal first sensor member and a distal first sensor member located on opposite sides of the first filter; and
   a flow control mechanism, interfaced with the first sensor for varying the operation of the variable vacuum motor according to the status of the first filter.

12. The smoke evacuator according to claim 11, further including a second filter proximal the first filter for removing particulates from smoke flowing through the evacuator, the second filter is in fluid communication with the distal end nozzle of the evacuator, the variable motor and the first filter.

13. The smoke evacuator according to claim 12, further including a second sensor attached to the second filter for detecting obstruction of the second filter, wherein the flow control mechanism is interfaced with the first sensor and the second sensor for varying operation of the variable vacuum motor according to the status of the first filter and the second filter.

14. The smoke evacuator according to claim 13, wherein the second sensor includes a proximal second sensor member and a distal second sensor member located on opposite sides of the second filter.

15. The smoke evacuator according to claim 11, further including an indicator interfaced with the first sensor for providing an indication of the first filter status.

16. The smoke evacuator according to claim 11, wherein the flow control mechanism, when activated by the first sensor, varies the speed of operation of the variable motor to maintain suction pressure at a constant level.

17. A filter adapted for use with a smoke evacuator, comprising:
- a filter body having a filter inlet port, a filter outlet port, and an internal filter medium;
- a fluid collection cap attached to the filter body and having a fluid baffle plate, a plurality of cap inlet ports, and a pressure sensor port.

18. The filter according to claim 17, wherein the fluid baffle plate is attached to the fluid collection cap to prevent fluid flowing through the cap inlet port from directly contacting the internal filter medium.

19. The filter according to claim 17, wherein the fluid collection cap further includes a first inlet port and a second inlet port.

20. The filter according to claim 17, wherein the first inlet port has a different diameter than the second inlet port.

* * * * *